United States Patent [19] [11] 4,162,893
Bühler et al. [45] Jul. 31, 1979

[54] PROCESS FOR DYEING HUMAN HAIR WITH DIAZO SALTS

[75] Inventors: Arthur Bühler, Rheinfelden; Alfred Fasciati, Bottmingen; Walter Hungerbühler, Riehen, all of Switzerland

[73] Assignee: Henkel Kommanditgesellschaft auf Aktien (Henkel KGaA) Dusseldorf-Holthausen, Fed. Rep. of Germany

[21] Appl. No.: 862,696

[22] Filed: Dec. 21, 1977

[30] Foreign Application Priority Data

Dec. 27, 1976 [CH] Switzerland .............. 16349/76

[51] Int. Cl.² ............................................. A61K 7/13
[52] U.S. Cl. .................................... 8/10.1; 8/10; 8/41 R; 8/44; 8/47
[58] Field of Search ................ 8/10.1, 10, 41 R, 44, 8/47

[56] References Cited

U.S. PATENT DOCUMENTS

| 1,718,882 | 6/1929 | Schwenk et al. ............... 8/47 |
| 1,727,920 | 9/1929 | Woetzel et al. ............... 8/47 |
| 1,877,318 | 9/1932 | Hoffa et al. ................. 8/44 |
| 1,914,441 | 6/1933 | Laska et al. ............... 8/47 X |
| 3,582,253 | 6/1971 | Berth et al. .............. 8/10.1 |
| 4,065,254 | 12/1977 | Buhler et al. ............. 8/47 X |

Primary Examiner—James O. Thomas, Jr.
Assistant Examiner—Vera C. Clarke
Attorney, Agent, or Firm—Hammond & Littell

[57] ABSTRACT

Described is a process for dyeing keratin-containing material with developing dyes by applying, successively in any desired sequence or simultaneously, to the keratin-containing material to be dyed, diazo salts and coupling components, and coupling these together, which process is characterized in that there are used coupling components of the formula

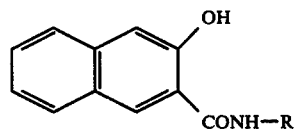

wherein R represents an unsubstituted or substituted aryl group.

7 Claims, No Drawings

PROCESS FOR DYEING HUMAN HAIR WITH DIAZO SALTS

The invention relates to a process for dyeing keratin-containing material, particularly human hair, with developing dyes.

Dyes used hitherto for dyeing human hair are in particular oxidation dyes, e.g. those based on p-phenylenediamine and benzidine. These dyes however have many disadvantages. Attempts have therefore been made to find for the dyeing of keratin-containing material, especially human hair, a dyeing process which eliminates these disadvantages.

For dyeing human hair there is thus known a dyeing process using developing dyes which are formed from a diazo salt and a coupling component, such as a benzene derivative or naphthol or 1-phenyl-3-methyl-pyrazol-5-one. These coupling components, particularly α- and β-naphthol, have however a low affinity for human hair and consequently are not particularly well suited for the intended purpose.

It has now been found that with use of a coupling component of the 2-hydroxy-naphthalene-3-carboxylic acid arylamide class it is possible in a surprising manner to overcome the stated disadvantages and furthermore to cover, with only one coupling component, the colour range from red to black by variation of the diazo component.

The process according to the invention for dyeing keratin-containing material with developing dyes by applying, successively in any desired sequence or simultaneously, to the keratin-containing material to be dyed, diazo salts and coupling components, and coupling these together, is characterised in that there is used a coupling component of the formula

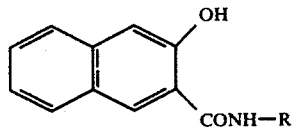

wherein R represents an unsubstituted or substituted aryl group.

As an aryl group, R represents for example a phenyl or naphthyl group (α- or β-). Substituents are for example: lower alkyl groups such as the methyl group; lower alkoxy groups such as the methoxy or ethoxy group; halogen such as, in particular, chlorine; the nitro group; the phenyl group, which for its part can be further substituted by the substituents mentioned. The aryl group R can however also be substituted by several identical or different substituents of the said kind. Furthermore, the radical R can be substituted by a further coupling component of the formula given above.

Examples of radicals denoted by the symbol "R" are given below:

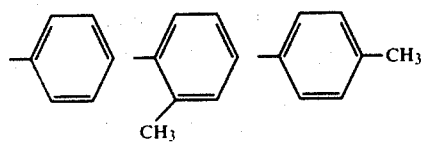

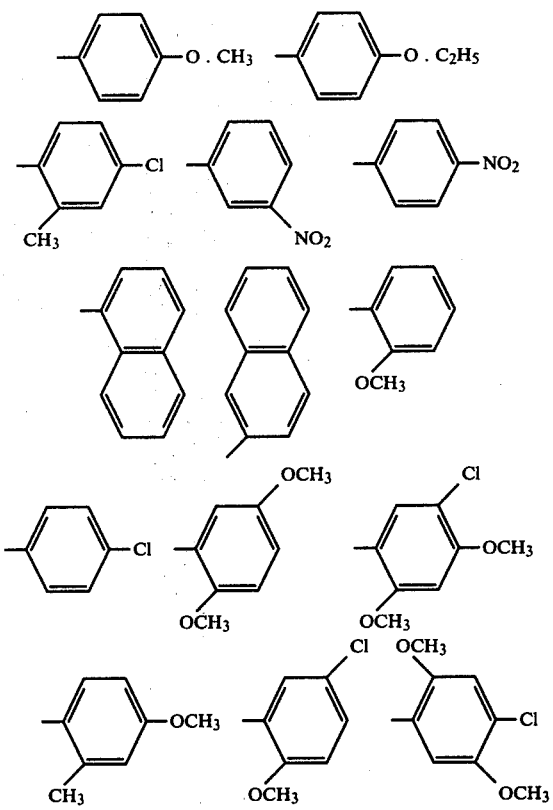

The preferred coupling component is that wherein R represents an unsubstituted phenyl group.

These coupling components are known and can be produced by known methods.

As diazo components necessary as the second component for the synthesis of the developing dye it is possible to use the diazotised aromatic or heteroaromatic amines known from the chemistry of azo compounds, particularly monoamines, especially aminobenzenes. The commercial stabilised diazonium compounds are particularly suitable for the process according to the invention.

As examples of applicable diazo components are listed the following in the form of the free amines:

2- or 3-chloroaniline, 2-, 3- or 4-nitroaniline, 2-methoxyaniline, 2,5-dichloroaniline, 3,5-di-trifluoromethylaniline, 2-chloro-5-trifluoromethylaniline, 2-methoxy-5-chloroaniline, 2-methyl-3-chloroaniline, 2-methyl-5-chloroaniline, 2-methyl-4-chloroaniline, 2-nitro-4-chloroaniline, 2-trifluoromethyl-4-chloroaniline, 2-nitro-4-methylaniline, 2-nitro-4-methoxyaniline, 2-nitro-4-ethoxyaniline, 2-methyl-4-nitroaniline or 2-methyl-5-nitroaniline, 2-methoxy-4-nitroaniline or 2-methoxy-5-nitroaniline, 2-ethylsulphonyl-5-trifluoromethylaniline, 3-ethylsulphonyl-6-methoxyaniline, 3-N,N-diethylaminosulphonyl-6-methoxyaniline, 3-N-n-butylaminosulphonyl-6-methoxyaniline, 1,4-diamino-2,6-dichlorobenzene, 2,4-dimethyl-3-nitroaniline, 2-methoxy-4-methyl-5-nitroaniline, 2-chloro-4-cyano-5-methylaniline, 2,5-dimethoxy-4-cyanoaniline, 4-phenylaminoaniline, 2-methoxy-4-phenylaminoaniline, 4-(4'-methoxyphenylamino)-aniline, 4',4''-diaminodiphenylamine, 2-phenylsulphonylaniline, 2,5-dimethoxy-4-phenylcarbonylamino-aniline, 2,5-diethoxy-4-phenylcarbonylamino-aniline, 2-(4'-chlorophenoxycarbonyl)-aniline, 3-benzylsulphonyl-6-methoxy-aniline, 2,5-dimethoxy-4-(4'-methylphenoxyacetylamino)-aniline, 2,5-diethoxy-4-(4'- or 2'-methylphenoxyacetylamino)-aniline, 2-phenoxy-5-chloroaniline, 2-(4'-chlorophenoxy)-5-chloroaniline, 4-aminoazobenzene, 3-methoxy-4-aminoazobenzene, 2',3- or 2,3'-dimethyl-4-aminoazobenzene, 2,5-dimethoxy-4'-nitro-4-aminoazobenzene, 2-methyl-5-methoxy-4,4'-diaminoazobenzene, 2-ethyl-5-methoxy-4-amino-4'-chloroazobenzene, 2-methyl-5-methoxy-4-amino-2'-nitro-4'-methylazobenzene, 2-amino-4-methoxy-5-methyl-2'-chloro-4'-nitroazobenzene, 2,5-dimethoxy-4-amino-2'-N,N-dimethylaminocarbonyl-4'-nitroazobenzene, 2,5-dimethoxy-4-amino-2',6'-dichloro-4'-nitroazobenzene, 2-chloro-4-benzoylamino-5-methoxyaniline, 2,4-dimethyl-5-benzoylaminoaniline, 2-N,N-diethylaminosulphonyl-4-benzoylamino-5-methoxyaniline, 2-methoxy-4-benzoylamino-5-methylaniline, 2,5-dimethoxy-4-benzoylaminoaniline, 2,5-diethoxy-4-benzoylaminoaniline, 4-(1'-naphthylazo)-aniline, 1-(2'-ethoxyphenylazo)-4-aminonaphthalene, 2-methyl-4-amino-5-ethoxy-4'-(4''-aminophenylamino)azobenzene, 1- or 2-aminonaphthalene, 3-benzoylamino-4-methoxyaniline and 1-aminoanthraquinone.

Preferred diazo components are aminobenzenes which are mono- or polysubstituted by halogen, particularly chlorine; lower alkyl, especially methyl; lower alkoxy, particularly methoxy or ethoxy; benzoylamino; alkoxyphenylamino, especially methoxyphenylamino; phenylamino; or by the phenylazo group, and this phenyl group is further substituted by the nitro group and/or lower alkyl, such as methyl.

Before diazotisation, these amines are converted into their salts, for example into the hydrochlorides or hydrosulphates, if necessary by heating, with moderately concentrated acid. The subsequent diazotisation can be performed by customary methods, e.g. by means of sodium nitrite and mineral acid, such as hydrochloric acid. Instead of using diazotised amines, it is also possible to use dye salts, i.e. stabilised diazonium compounds. Suitable stabilisers and separating reagents for the dye salts are: metal chlorides such as $ZnCl_2$, $CdCl_2$, $CoCl_2$ or $MnCl_2$, which can be separated with the diazo compound as a complex from the aqueous solution, aromatic sulphonic acids which can be used as free acids or as alkali salts, and which form with diazonium compounds true salts, especially naphthalene-disulphonic acids, hydrofluoboric acid, which likewise forms with diazo compounds true salts, and acylaminoaryl-sulphonic acids, such as acetylsulphanilic acid. In some cases, also the diazonium chlorides or acid sulphates themselves can be separated and used. The stabilised diazonium salts or diazoamino salts contain also inert salts. With the use of dye salts, an addition of alkali-binding agents, such as acetic acid, formic acid, sodium acetate/acetic acid, chromium acetate or mono- or disodium phosphate, is in some cases necessary, since dye salts are broken down by alkali action.

The application of the diazo and coupling components to the keratin-containing material, particularly to human hair, is effected preferably in two stages, in such a manner that firstly one of the two components of the developing dye, preferably the coupling component, is applied to the material, and is subsequently coupled on the material with the diazo component. It is however also possible to apply the coupling component and diazo component simultaneously to the hair. In this respect, the conditions under which the process is performed depend on the nature of the keratin-containing material to be dyed. The coupling itself occurs in the alkaline pH range of about 7 to 12, preferably up to pH 11.

If living material is involved, that is, human or animal hair, the coupling and diazo components are applied at about 15° to 40° C., preferably at room temperature, e.g. by spraying or by applying in the form of an aqueous solution, nonionic cream, emulsion or gel. The reaction time in the case of the component first applied is about 1 to 25, preferably 2 to 10, minutes. The material is then optionally rinsed and intermediately dried or, conversely, firstly intermediately dried and then rinsed; and the second component is subsequently applied, preferably in the same manner. The time required for the coupling reaction is about 0.5 to 20 minutes, preferably 1 to 10 minutes. The dyed keratin-containing material, e.g. human hair, is afterwards rinsed, optionally with the addition of preferably nonionic surface-active agents, and subsequently dried.

Dead material, such as skins, furs, feathers, or wigs made from human hair, are impregnated with solutions of the coupling or diazo components preferably by immersion in these solutions. The temperature for this can be, e.g., up to 60° C. After impregnation with the first component, the keratin-containing material can be optionally squeezed out or centrifuged before it is impregnated with the second component necessary for the formation of the dye.

An aqueous solution of the coupling component is preferably prepared by adding the coupling component to water, optionally together with a solubility-promoting agent, such as alcohol, and adding alkali, e.g. ammonia or aqueous sodium hydroxide solution, until a clear solution is obtained. The diazo components, which are preferably used as stabilised diazonium salts, are employed as aqueous solutions.

Coupling and diazo components are preferably used in approximately equal molar amounts. An excess of up to about 100% of one component, preferably the diazo component, is not harmful: indeed it frequently leads to good results.

In the process according to the invention, the coupling and diazo components can be used as homogeneous substances. Since however in the dyeing of keratin-containing material, particularly human hair, mixed shades are often desired, it is also possible to use mixtures of the coupling components and/or of the diazo components.

The concentration of the solutions is generally between 0.1 and 10%, preferably between 0.5 and 5%, of coupling or diazo component, relative to the total composition.

For producing creams, emulsions or gels, the solutions of the coupling and diazo components, respectively, are provided with the customary additives, such as surface-active agents, preferably of a nonionic nature, such as fatty acid ethanolamides, polyalcohols (ethylene oxide polymers with a degree of polymerisation of 200 to 1000) or addition products of ethylene oxide with fatty acids, with fatty alcohols, with fatty amines or with alkylphenols. And also anion-active compounds can be added, such as alkylsulphonates, alkylbenzenesulphonates and fatty alcohol sulphates. Creams of this kind, particularly those with the coupling component, are storage-stable at a temperature of about −10° C. to +45° C. for about 2 months.

Furthermore, the solutions, creams, emulsions or gels can contain further additives, for example thickening agents such as starch or methylcellulose, Vaseline ®, higher fatty alcohols, paraffin oils, fatty acids, as well as perfume oil or hair tonics, such as pantothenic acid or cholesterol. These additives are used in the customary amounts.

A preferred method of application of the coupling and diazo components to human hair consists of pre-shampooing the hair with the coupling component in shampoo form, especially with a cream-like shampoo, and, without intermediate rinsing, after-shampooing with the diazo component, likewise in shampoo form; or alternatively applying both components in cream form.

The process according to the invention is suitable in particular for shading or dyeing; it can however be used also for overdyeing, especially for overdyeing human hair.

There are obtained by this process deeply coloured dyeings having good properties in service. By properties in service are meant, e.g.: fastness to washing, the possibility of turning dyed hair blonde (oxidise with $H_2O_2$), fastness to cold setting, fastness to rubbing, fastness to light, absorption of the components in the case of damaged hair, fastness to perspiration and behaviour with regard to permanent waving.

The process according to the invention can be carried out both on untreated keratin-containing material, particularly on human hair, and on treated hair, such as on bleached or permanently-waved hair.

The azo dyes developed on the keratin-containing material are known or can be produced by methods known per se.

It is possible by the process according to the invention to produce with only one coupling component shades from red to black with variation of the diazo component. The process of the invention moreover avoids the use of oxidation dyes, and can be performed at room temperature. The process according to the invention is furthermore distinguished by the ease with which it can be carried out, and by the fact that a chemically definable dye is formed, whereas with oxidation dyes there are obtained obscure indefinable mixtures of completely to only partially oxidised amines, mixed with intermediate products.

The following Examples serve to illustrate the invention. Percentages are percent by weight, parts are parts by weight and temperatures are in degrees Centigrade. The diazo components (amines) used were employed as stabilized diazonium compounds in commercial form.

EXAMPLES 1–18

There is prepared a 1% aqueous solution of the coupling component of the formula

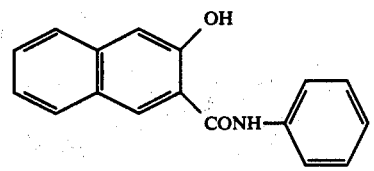

by introducing this into distilled water, and dissolving it by the addition of 2% ethanol and 1% sodium hydroxide solution.

A bundle of grey human hair weighing 0.3 g is immersed in 50 ml of this solution, and is left for 15 minutes at room temperature in this solution (pH value about 11).

The bundle of hair is subsequently removed from the solution; the bundle is squeezed out briefly with a glass rod, and is then immersed for 5 minutes at room temperature in a 1% aqueous solution of one of the stabilized diazonium compounds listed in the following Table; it is subsequently rinsed under running water and dried in air.

Dyed hair which displays the respective shade given in column III of the Table and which has good properties in service is obtained.

Table

| I | II | III |
|---|---|---|
| Ex. | Stabilized diazonium compounds in the form of the free amine | Shade on human hair |
| 1 | 2-chloroaniline (NH₂, Cl) | scarlet |
| 2 | phenyl-CONH- substituted 2,5-dimethoxyaniline (OCH₃, NH₂, OCH₃) | reddish-black |
| 3 | CH₃O—C₆H₄—NH—C₆H₄—NH₂ | black |
| 4 | 2,5-dichloroaniline (NH₂, Cl, Cl) | red |

Table-continued
| Ex. | Stabilized diazonium compounds in the form of the free amine | Shade on human hair |
|---|---|---|
| 5 | 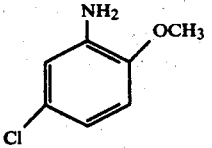 | carmine red |
| 6 | 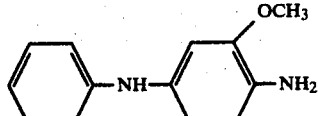 | blackish-blue |
| 7 | 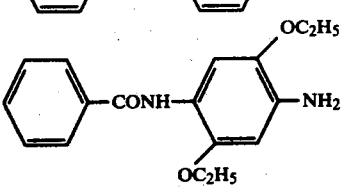 | dark blue |
| 8 | 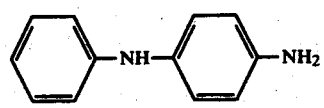 | bluish-black |
| 9 | 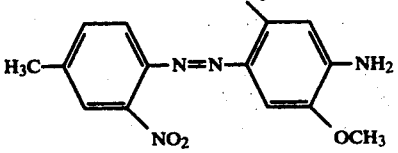 | currant shade |
| 10 | 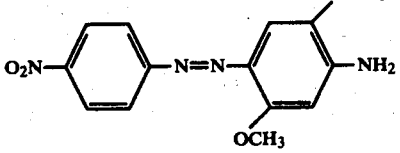 | black |
| 11 | 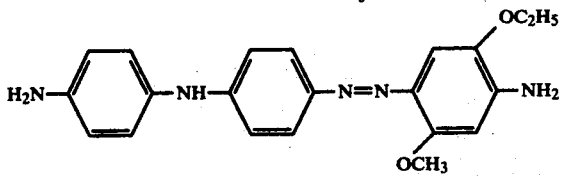 | black |
| 12 | 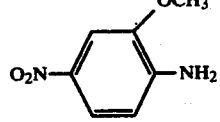 | red |
| 13 | 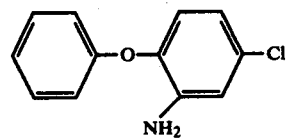 | scarlet |
| 14 | 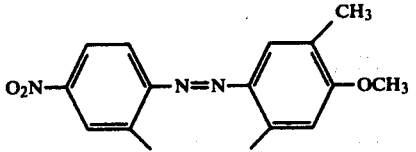 | brown |
| 15 | 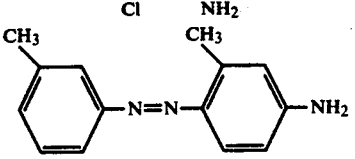 | reddish-brown |

Table-continued

| Ex. | II Stabilized diazonium compounds in the form of the free amine | III Shade on human hair |
|---|---|---|
| 16 | stabilized diazonium compound from Example 1 + stabilized diazonium compound from Example 7 (1:1) | brown |
| 17 | stabilized diazonium compound from Example 5 + stabilized diazonium compound from Example 8 (1:1) | brown |
| 18 | stabilized diazonium compound from Example 6 + stabilized diazonium compound from Example 10 (1:1) | black |

EXAMPLE 19

A cream emulsion is prepared by adding 1 part of the coupling component of the formula

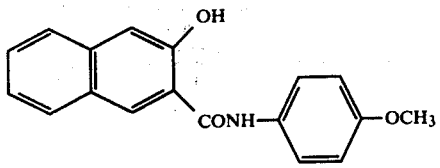

to 75 parts of water, dissolving it by the addition of ammonia, subsequently adding 10 parts of fatty alcohol sulphate (sodium salt, chain length $C_{12}$–$C_{18}$) as well as 10 parts of fatty alcohol (chain length $C_{12}$–$C_{18}$), and making up to 100 parts with water.

This cream emulsion is applied at room temperature to a bundle of grey human hair by rubbing in, and leaving it to react for 15 minutes. The hair is rinsed briefly with water, and there is then applied, by rubbing in, an emulsion which has been obtained by working 1 part of the amine of the formula

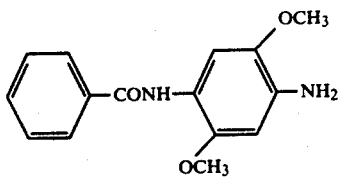

in the form of a stabilized diazonium compound, as well as 10 parts of the above-used fatty alcohol and fatty alcohol sulphate, into 79 parts of water.

A reaction time of 5 minutes is allowed; the hair is then thoroughly rinsed, with the addition of a customary washing agent, to obtain hair which is dyed violet and which has good properties in service.

EXAMPLE 20

A bundle of bleached strands of hair is dyed as follows: The coupling component of the formula

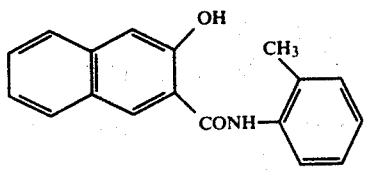

is applied, in a nonionic cream form containing 2 percent by weight of coupling component, at 27° and at a pH value of 9.5 for 10 minutes to the strands of hair. The excess cream is then removed as far as possible by wiping off, and the strands of hair pretreated in this manner are intermediately dried. After intermediate drying, the diazo component, produced from the amine of the formula

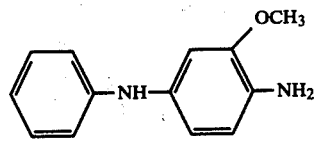

is applied as an aqueous solution containing 2% of diazo component, at the same temperature but with a shorter reaction time. The hair is then washed and dried.

Hair which is dyed bluish-black and which has good fastness properties in service is obtained.

EXAMPLE 21

10 g of a chrome tanned sheepskin, shorn to about 15 mm, is wetted back for one hour, in a dyeing drum, at 40° in 200 ml of an aqueous solution containing 0.2 g of anhydrous sodium carbonate, 0.2 g of 24% ammonia and 0.1 g of a nonionic detergent; the material is subsequently rinsed and centrifuged. This material is introduced into 200 ml of a liquor at 25°, obtained by dissolving 0.1 g of the coupling component of the formula

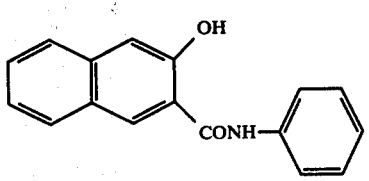

and 0.05 g of sodium carbonate with the subsequent addition of 0.1 ml of an 85% aqueous formic acid, and is treated for 30 minutes at this temperature in a dyeing drum. The material is afterwards rinsed and centrifuged. The sheepskin is then immersed in 200 ml of a liquid at 25°, which contains 0.4 g of the diazo component produced from the amine of the formula

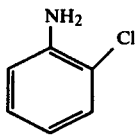

and 0.1 g of a nonionic detergent, and treated for 30 minutes at 25°; it is subsequently rinsed, centrifuged and dried.

A sheepskin dyed in a scarlet shade is obtained.

EXAMPLES 22–27

If the process is carried out as described in Example 1 except that instead of the coupling component used therein the same amount of the coupling components given in the following Table in column II is used, there is obtained dyed hair which has the respective shade shown in column III and which has good properties in service.

1. A process for dyeing human hair with developing dyes which comprises applying to said hair, at temperatures of from about 15° to 40° C., an effective amount for dyeing of aqueous solutions of diazo salts and coupling components successively in any desired sequence, or simultaneously, and coupling said diazo salts and coupling components with each other, wherein the coupling component is a 2-hydroxy-naphthalene-3-carboxylic acid amide of the formula

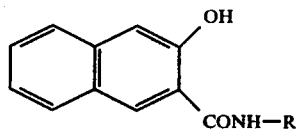

wherein R represents a member selected from the group consisting of an unsubstituted aryl group and a substituted aryl group.

2. The process of claim 1 wherein R represents a member selected from the group consisting of

| Ex. | Coupling component | Shade on human hair |
|---|---|---|
| 22 | [2-hydroxy-naphthalene-3-carboxylic acid amide of 2-methoxyphenyl] | scarlet |
| 23 | [2-hydroxy-naphthalene-3-carboxylic acid amide of 4-methoxyphenyl] | " |
| 24 | [2-hydroxy-naphthalene-3-carboxylic acid amide of 4-chlorophenyl] | " |
| 25 | [2-hydroxy-naphthalene-3-carboxylic acid amide of 2,4-dimethoxy-5-chlorophenyl] | " |
| 26 | [2-hydroxy-naphthalene-3-carboxylic acid amide of 2-methyl-4-chlorophenyl] | " |
| 27 | [bis(2-hydroxy-naphthalene-3-carboxylic acid amide) of 3,3'-dimethoxybenzidine] | red |

We claim:

(1) phenyl,
(2) α-naphthyl,
(3) β-naphthyl,
(4) components (1), (2), or (3) substituted with substituents selected from the group consisting of lower alkyl groups, lower alkoxy groups, halogens, nitro groups and mixtures thereof,
(5) components (1), (2) or (3) substituted with phenyl,
(6) components (1), (2) or (3) substituted with phenyl containing substituents selected from the group consisting of lower alkyl groups, lower alkoxy groups, halogens, nitro groups and mixtures thereof, and
(7) biphenyl having the formula

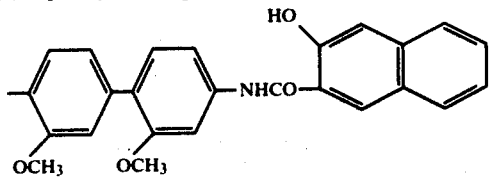

3. Process according to claim 2, wherein R represents phenyl.

4. Process according to claim 1, wherein the diazo salts used are stabilised diazonium compounds of monoamines.

5. Process according to claim 4, wherein the diazo salts used are stabilised diazonium compounds of aminobenzene derivatives.

6. Process according to claim 5, wherein the aminobenzene derivatives used are aminobenzenes which are mono- or poly-substituted by halogen; lower alkyl; lower alkoxy; benzoylamino; alkoxyphenylamino; phenylamino; or by the phenylazo group, and this phenyl group is further substituted by the nitro group or lower alkyl.

7. Process according to claim 1 wherein there is firstly applied the coupling component and subsequently the diazo salt to the human hair to be dyed.

* * * * *